US008507547B2

(12) United States Patent
Asami et al.

(10) Patent No.: US 8,507,547 B2
(45) Date of Patent: Aug. 13, 2013

(54) ANTI-FATIGUE AGENTS AND ORAL COMPOSITIONS CONTAINING ANDROGRAPHOLIDE AS ACTIVE INGREDIENT

(75) Inventors: Sumio Asami, Osaka (JP); Kayo Saito, Osaka (JP); Akifumi Maeda, Osaka (JP); Norifumi Tateishi, Osaka (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 512 days.

(21) Appl. No.: 12/602,006

(22) PCT Filed: May 30, 2008

(86) PCT No.: PCT/JP2008/060011
§ 371 (c)(1),
(2), (4) Date: Nov. 25, 2009

(87) PCT Pub. No.: WO2008/149802
PCT Pub. Date: Dec. 11, 2008

(65) Prior Publication Data
US 2010/0144866 A1    Jun. 10, 2010

(30) Foreign Application Priority Data

May 31, 2007   (JP) ................ 2007-144623

(51) Int. Cl.
*A01N 43/02*    (2006.01)
*A01N 43/08*    (2006.01)
*A61K 31/335*   (2006.01)
*A61K 31/34*    (2006.01)

(52) U.S. Cl.
USPC ........................... 514/449; 514/461; 514/468

(58) Field of Classification Search
USPC .................. 514/183, 449, 461, 468
See application file for complete search history.

(56) References Cited

U.S. PATENT DOCUMENTS

| 6,326,137 | B1 * | 12/2001 | Hong et al. | 435/5 |
| 6,410,590 | B1 | 6/2002 | Nanduri et al. | |
| 6,664,287 | B2 * | 12/2003 | Avery et al. | 514/436 |
| 2003/0044512 | A1 | 3/2003 | Watson et al. | |
| 2003/0138509 | A1 | 7/2003 | Pushpangadan et al. | |
| 2006/0063831 | A1 | 3/2006 | Orozco et al. | |
| 2006/0223785 | A1 * | 10/2006 | Liu et al. | 514/100 |
| 2007/0196508 | A1 | 8/2007 | Heuer et al. | |

FOREIGN PATENT DOCUMENTS

| CN | 1437939 A | 8/2003 |
| CN | 1962650 | 5/2007 |
| JP | 08-034740 | 2/1996 |
| JP | 2000-103718 | 4/2000 |
| JP | 2003-522166 | 7/2003 |
| JP | 2006 137730 | 6/2006 |
| JP | 2007-176934 | 7/2007 |
| WO | WO 01/00194 A2 | 1/2001 |
| WO | 03/080062 | 10/2003 |
| WO | 2007/095718 | 8/2007 |

OTHER PUBLICATIONS

Kligler B. et al., "*Andrographis Paniculata* for the Treatment of Upper Respiratory Infection: A Systematic Review by the Natural Standard Research Collaboration", Journal of Science and Healing, Elsevier, Jan. 2006, vol. 2, No. 1, pp. 25-29.
Extended European Search Report mailed Nov. 11, 2010, for European Patent Application No. 08777022.8; 7 pages.
Rakshamani Tripathi et al., "Modulation of Oxidative Damage by Natural Products", Food Chemistry, vol. 100, 2007, pp. 81-90.
Aruna Kapil et al., "Antihepatotoxic effects of Major Diterpenoid Constituents of *Andrographis Paniculata*", Biochemical Pharmacology, vol. 46, No. 1, 1993, pp. 182-185.
Chuyaku Daijiten, vol. 3, the First Impression of the First Edition issued on Dec. 10, 1985.
International Search Report mailed Aug. 26, 2008 in International Application No. PCT/JP2008/060011 filed May 30, 2008.
Caceres D D et al., "Use of visual analogue scale measurements (VAS) to asses the effectiveness of standardized *Andrographis paniculata* extract SHA-10 in reducing the symptoms of common cold. A randomized double blind-placebo study", Pytomedicine: international journal of pytotherapy and phytopharmacology, 1999, vol. 6, No. 4, pp. 217-223. (Abstract) MEDLINE [online]; U.S. National Library of Medicine and the National Institutes of Health [retrieved on Aug. 11, 2008] Retrieved from: STNInt., Medline Accession No. 2000056879, PubMED ID: 10589439.
European Official Action issued in European No. EP 08 777 022.8-2123 dated Mar. 13, 2012.
Cáceres et al., "Use of visual analogue scale measurements (VAS) to asses the effectiveness of standardized *Andrographic paniculata* extract SHA-10 in reducing the symptoms of common cold. A randomized double blind-placebo study," Phytomedicine, 1999, vol. 6, No. 4, pp. 217-223.
"Food Processing and Ingredients," Feb. 2007, vol. 42, No. 2, pp. 22-31 (partial English-language translation).

* cited by examiner

*Primary Examiner* — Yong Chong
(74) *Attorney, Agent, or Firm* — Drinker Biddle & Reath LLP

(57) ABSTRACT

Disclosed is a composition which is safe for a human body and an animal, can be ingested continuously on a daily basis, has an anti-fatigue activity, and is effective for the prevention or treatment of a disease or condition associated with fatigue. Specifically disclosed is an anti-fatigue agent comprising andrographolide optionally together with an α-lipoic acid as an active ingredient(s). Also disclosed is a novel oral composition comprising andrographolide and an α-lipoic acid. The anti-fatigue agent and the oral composition are useful for the prevention or treatment of chronic fatigue syndrome, overfatigue, physical fatigue, mental fatigue and organ fatigue.

5 Claims, 4 Drawing Sheets

ANTI-FATIGUE AGENTS AND ORAL COMPOSITIONS CONTAINING ANDROGRAPHOLIDE AS ACTIVE INGREDIENT

CROSS REFERENCE TO RELATED APPLICATIONS

This application is the National Stage of International Application No. PCT/JP2008/060011, filed May 30, 2008, and claims benefit of Japanese Application No. 2007/144623, filed May 31, 2007, each of which is incorporated by reference in its entirety.

TECHNICAL FIELD

The present invention relates to anti-fatigue agents containing andrographolide as an active ingredient. In particular, the present invention relates to pharmaceutical compositions, food, and drink that contain andrographolide as an active ingredient and are used to prevent or treat fatigue-related illnesses or conditions. The present invention also relates to new oral compositions containing andrographolide and alpha-lipoic acid as active ingredients, and anti-fatigue agents that contain andrographolide and alpha-lipoic acid as active ingredients and are used to prevent or treat fatigue-related illnesses or conditions.

BACKGROUND ART

Fatigue, generally with feeling of tiredness and lassitude as prominent symptoms, is a condition that is also accompanied by diverse symptoms such as sleep disorder and hypobulia, and many people in today's society deal with this phenomenon. Feeling of tiredness and lassitude are one of the important alarm signals that give warnings about abnormality in body. Even a person who is in a normal state comes to feel fatigued when, for instance, doing hard exercise, working for a long time, or being under extreme stress. This sort of physiological fatigue is generally cured to a normal state if the body is rested, and does not remain for a long time. People in today's society, however, tend to work long hours and be under extreme stress, and have difficulty in taking an adequate rest. This often makes it difficult to recover from feeling of tiredness and lassitude. There is even a report saying that the number of people who suffer from chronic fatigue has increased over the last 14 years and that the nature of fatigue has changed (Non-patent Literature 1).

Meanwhile, in today's Japan, "death by overload", defined as a sudden death from long hours of overwork, has been a huge social issue. Although death by overload has been recognized as a considerably important issue medically, economically, and socially, the pathogenic mechanism of death by overload has remained largely unexplained. Accumulation of mental and/or physical fatigue is considered as the main factors that cause death by overload.

Further, an illness called chronic fatigue syndrome (CFS) has drawn attention as an intractable disease. This is an illness brought up in 1988 by the US Center for Disease Control and Prevention (CDC). Specifically, this illness causes a person leading a healthy life to suddenly feel strong general tiredness for no known reason and brings mental and/or physical symptoms such as low grade fever, cephalalgia, lymph node swelling, muscle ache, arthralgia, diminished ability to think, diminished ability to concentrate, and sleep disorder. This state continues for a long time to cause the person to become unable to lead a healthy social life. In Japan, professional study groups of the Ministry of Health and Welfare just started surveys on death by overload since about 1991. Neither the cause of death by overload has been explained, nor diagnostic criteria has been established. As death by overload has become a social issue today, prompt clarification of the cause of chronic fatigue syndrome has been demanded. However, as mentioned earlier, even the diagnostic criteria have not been established, yet.

Fatigue includes those from mental cause and those from physical cause. Since fatigue from mental cause and fatigue from physical cause are in many cases closely related, it is said that they are difficult to distinguish. When physical fatigue persists, mental fatigue such as general lassitude and feeling of weakness gradually comes to be felt. At the same time, ability to concentrate diminishes, disinclination occurs, and/or drowsiness is induced. Sometimes physical and/or mental fatigue cause visceral functions to decline, that is to say, visceral fatigue is induced. Relation between sleep disorder and fatigue has drawn attention; staying up all night results in fatigue accompanied by discomfort, and this, in many cases, negatively affects everyday living.

In view of the foregoing situation, so-called "anti-fatigue substances" have been proposed for reduction of fatigue and recovery from fatigue to a normal state. There have been reports on, for instance, the body strength enhancing action of certain types of amino acid compositions (Patent Literature 1), the body strength enhancing action of L-carnitine and histidine-related dipeptides (Patent Literature 2), and the endurance improving action, the muscular tissue strengthening action, and the muscle fatigue recovery promoting action of crataegus fruit extracts (Patent Literature 3). Patent Literature 4 discloses nutritional supplementary compositions containing food ingredients (including ascorbic acids) having insulin supersecretion amino acid and antioxidative action to supply nutrition at the time of exhaustion from exercise or at the time of fatigue. There is a report saying that ascorbic acid is effective for symptomatic therapy to treat chronic fatigue syndrome (Non-patent Literature 2). Further, Patent Literature 5 discusses that acyl carnitine in blood serum of a patient with chronic fatigue syndrome is decreased and that administration of acetyl-L-carnitine is effective for treatment of disorder in acyl carnitine metabolism (Patent Literature 5).

Regarding andrographolide, it is said that an intake of 200 mg of Andrographis paniculata, which is a plant known to contain andrographolide, per day produces an effect of preventing a cold during the cold months, and an intake of 1200 mg of Andrographis paniculata per day reduces symptom of a cold. There have been further reports saying that andrographolide and derivatives of andrographolide can be used as anticancer agents, antiviral drugs, antimalaria drugs, antibacterial drugs, hepatoprotectors, immunomodulators, and the like (Patent Literature 6), that andrographolide has effect of regulating functions of platelet activating factor acetyl hydrolase (Patent Literature 7), and that andrographolide has effect of increasing reduced liver glutathione activity due to oxidative stress (Non-patent Literature 3). However, neither action against fatigue stress nor anti-fatigue action has been reported.

Patent Literature 1: Japanese Unexamined Patent Publication No. 124473/1997 (Tokukaihei 9-124473)
Patent Literature 2: Japanese Unexamined Patent Publication No. 046021/2001 (Tokukai 2001-046021)
Patent Literature 3: Japanese Unexamined Patent Publication No. 47381/1996 (Tokukaihei 8-47381)
Patent Literature 4: Japanese Unexamined Patent Publication No. 327435/1994 (Tokukaihei 6-327435)

Patent Literature 5: Japanese Unexamined Patent Publication No. 26987/1996 (Tokukaihei 8-26987)
Patent Literature 6: Published Japanese Translation of PCT International Publication for Patent Application, Publication No. 522166/2003 (Tokuhyo 2003-522166)
Patent Literature 7: Japanese Unexamined Patent Publication No. 176934/2007
Non-patent Literature 1: Science of Fatigue (Hiro no kagaku), Masayasu Inoue, Hirohiko Kuratsune, and Yasuyoshi Watanabe, eds., Kodansha, pp. 222-228, 2001
Non-patent Literature 2: In Vivo (1996) November-December; 10(6): 585-96
Non-patent Literature 3: Biochemical Pharmacology (1993) Vol. 46, No. 1, pp. 182-185

DISCLOSURE OF THE INVENTION

Problems to be Solved by the Invention

To live a health everyday life, compositions having anti-fatigue action are demanded not only by people who lead a special life, such as athletes, but also people who lead a normal life. Such compositions are also demanded for animals including animals for races such as racehorses, livestock, animals at facilities such as a zoo, and pet animals. There are demands especially for compositions that are effective against not only physical fatigue but also mental fatigue, organ fatigue, and fatigue of combinations thereof. However, conventional anti-fatigue substances target mainly on muscle fatigue from exercise and contain caffeine and/or ethyl alcohol to bring excitement, insomnia, and the like. Many people who feel fatigue say that they do not recover from fatigue even if they take an overnight rest. There is, therefore, a possibility that they may reach a pathological fatigue state, such as overwork state and chronic fatigue syndrome, if the fatigue is left untreated. However, when people are able to manage to lead their everyday living, they tend not to spare their time to go to a hospital but leave the fatigue untreated, since they are busy with their everyday life. Thus compositions that can be taken repeatedly on a regular basis have been demanded.

The present invention has as an object to provide a composition that is safe to humans, animals, and the like, can be taken repeatedly on a regular basis, has anti-fatigue action, and is effective for preventing or treating fatigue-related illnesses or conditions.

Means for Solving the Problems

The inventors of the present invention have diligently searched various food compositions to solve the problem. Consequently, they found that andrographolide had anti-fatigue action, concretely, action to reduce mental and organ fatigue stress, action to promote recovery, action to prevent physical fatigue, action to reduce stress, action to promote recovery, action associated with the foregoing action, such as improvement in endurance and enhancement in body strength, and the like. They also found that the anti-fatigue action was produced no matter whether it was administered before fatigue stress, during fatigue stress, or after fatigue stress. Furthermore, they also found that the anti-fatigue action was enhanced by a combination of andrographolide and alpha-lipoic acid, compared with that obtained by andrographolide administered alone and that obtained by alpha-lipoic acid administered alone. With the foregoing findings, they completed the present invention.

Specifically, the present invention provides an anti-fatigue agent containing andrographolide as an active ingredient.

The present invention further provides the anti-fatigue agent in the form of a pharmaceutical composition, a food, or a drink for preventing or treating fatigue-related illnesses or conditions.

The present invention further provides the anti-fatigue agent against the fatigue-related illnesses or conditions selected from the group consisting of a chronic fatigue syndrome, a death by overload, overwork, physical fatigue (e.g., muscle fatigue), mental fatigue (e.g., fatigue from lack of sleep), and organ (internal organs, especially liver and spleen) fatigue, preferably a combination of two or more of them.

The present invention further provides the anti-fatigue agent comprising, per daily amount of the anti-fatigue agent to be taken by an animal including a human, 0.01-500 mg of andrographolide per kilogram of body weight (preferably 0.1-50 mg per kilogram of body weight, more preferably 0.1-10 mg per kilogram of body weight, especially preferably 0.25-10 mg per kilogram of body weight).

The present invention further provides the anti-fatigue agent comprising, per daily amount of the anti-fatigue agent to be taken by a human (adult), 0.1-100 mg of andrographolide (preferably 0.1-50 mg, more preferably 0.1-10 mg, especially preferably 0.25-10 mg).

The anti-fatigue agent can be taken either a single time or multiple times (e.g. two or three times) per day. The present invention further provides the anti-fatigue agent comprising, per daily amount of the anti-fatigue agent to be taken by a human (adult), 0.03-50 mg (preferably 0.05-25 mg, more preferably 0.03-5 mg, especially preferably 0.13-5 mg).

The present invention further provides an oral composition comprising andrographolide and alpha-lipoic acid as anti-fatigue active ingredients and producing excellent anti-fatigue action, compared with that containing andrographolide alone or alpha-lipoic acid alone as a single active ingredient. The oral composition of the present invention can be used as an anti-fatigue agent.

The present invention further provides the anti-fatigue agent against fatigue-related illnesses or conditions from mental fatigue or lack of sleep.

The present invention further provides the anti-fatigue agent that is to be taken orally.

Further, the present invention relates to use of either andrographolide or andrographolide and alpha-lipoic acid to produce pharmaceutical compositions, food, or drink for preventing or treating fatigue-related illnesses or conditions.

The present invention further relates to a method for preventing or treating fatigue-related illnesses or conditions, which method includes administration of either andrographolide or andrographolide and alpha-lipoic acid.

The present invention further provides pharmaceutical compositions, food, or drink, containing either andrographolide or andrographolide and alpha-lipoic acid as active ingredients and having anti-fatigue action.

The present invention further provides pharmaceutical compositions, food, or drink, characterized by containing the anti-fatigue agent and used for preventing or treating fatigue-related illnesses or conditions.

The present invention further provides the anti-fatigue agent in the form of a capsule, a supplement, or a drink.

Further, the present invention relates to a method for reducing mental fatigue, physical fatigue and/or organ fatigue stress, which method includes administering either andrographolide or andrographolide and alpha-lipoic acid at least once during fatigue stress.

The present invention further relates to a method for promoting recovery from mental fatigue and/or physical fatigue (especially physical fatigue), which method includes administering either andrographolide or andrographolide and alpha-lipoic acid at least once after fatigue stress.

The present invention further relates to a method for preventing or reducing physical fatigue (muscle fatigue) stress, which method includes administering either andrographolide or andrographolide and alpha-lipoic acid at least once before fatigue stress.

Advantages of the Invention

The anti-fatigue agent of the present invention, concretely pharmaceutical compositions, food, or drink for preventing or treating fatigue-related illnesses or conditions, has excellent anti-fatigue action, and administration of the anti-fatigue agent of a small amount to humans or animals produces the effect. Therefore, the anti-fatigue agent is safe. Thus the anti-fatigue agent of the present invention can be taken repeatedly on a regular basis. Since the anti-fatigue agent of the present invention can be administered at any time, it can be taken in when fatigue is felt in order to promote quick recovery from fatigue. It is also possible to take in the anti-fatigue agent of the present invention before working or doing sports to prevent fatigue. Improvement in endurance is also expected by taking in the anti-fatigue agent of the present invention before or during sports. Prompt production of the effect is also expected. Taking in the anti-fatigue agent of the present invention on a regular basis prevents physical, mental, and/or organ fatigue-related illnesses or conditions. The anti-fatigue agent of the present invention also prevents wrinkles and skin damage caused by fatigue.

In an aspect of the present invention in which both andrographolide and alpha-lipoic acid are used as active ingredients, the anti-fatigue action improves synergistically, compared with that obtained by andrographolide alone and that obtained by alpha-lipoic acid alone. The wording synergistic improvement in anti-fatigue action means that effect (synergistic effect) that can be obtained by neither andrographolide alone nor alpha-lipoic acid alone is obtained. For instance in Example 5 in this Specification, when a swimming time calculated by subtracting a swimming time of a water-immersed control group from a swimming time of a normally-reared group was 100%, increase rates of the respective groups were as follows. The swimming time of the group to which andrographolide was administered alone increased by 5%, and the swimming time of the group to which alpha-lipoic acid was administered alone increased by 13%. The swimming time of the group to which the combination of andrographolide and alpha-lipoic acid was administered increased by 51%. It can be said therefrom that the combined use of the two ingredients improved the action synergistically.

EMBODIMENT OF THE INVENTION

Andrographolide

Figure 1:
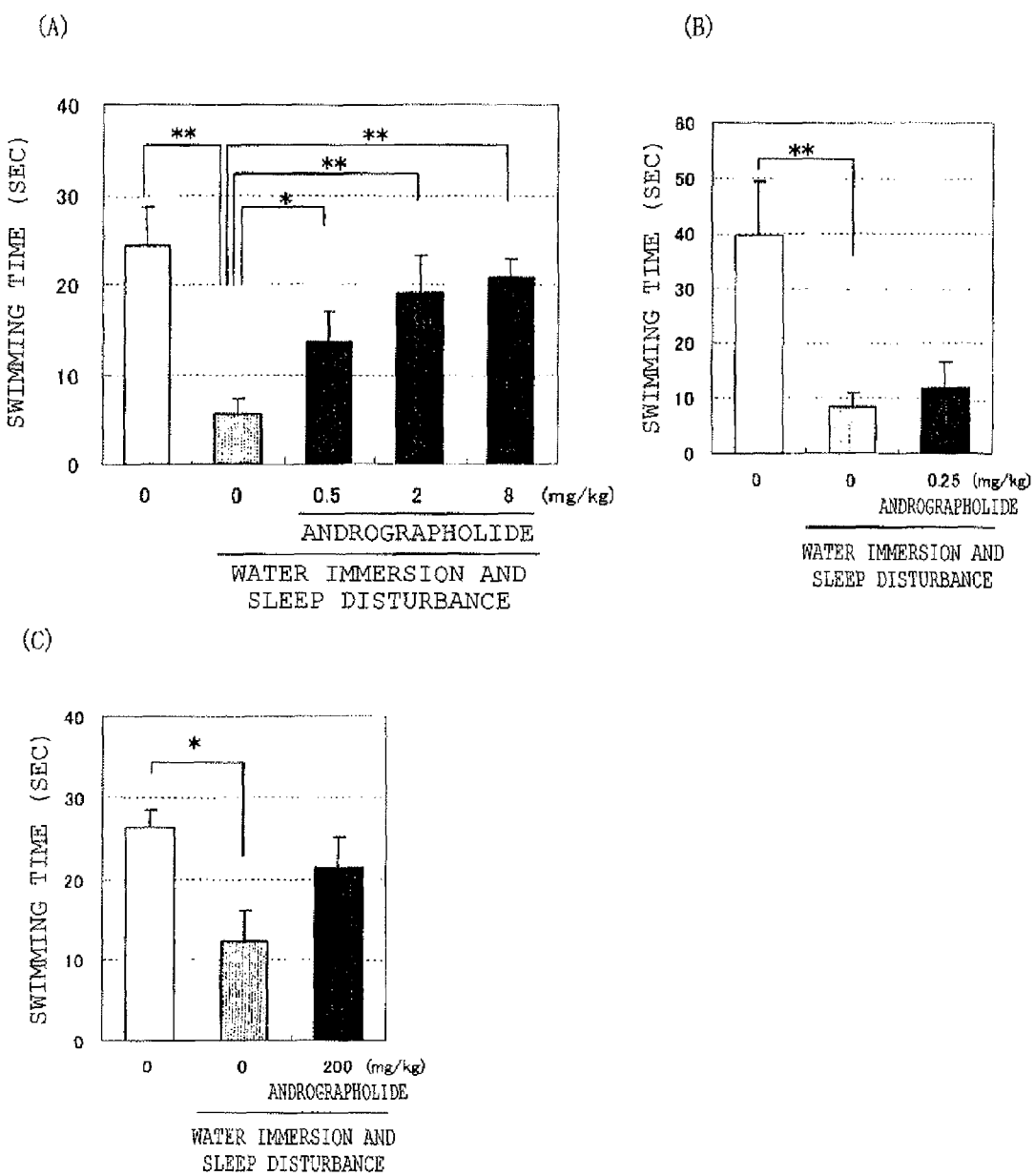
FIG. 1 is a graph showing a relationship between administration of andrographolide (FIG. 1(A): 0.5, 2.0, 8.0 mg per kilogram of body weight per day, FIG. 1(B): 0.25 mg per kilogram of body weight per day, FIG. 1(C): 200 mg per kilogram of body weight per day) and a swimming time after water immersion in a weight-loaded forced swimming test in Example 1.

Andrographolide (3-[2-decahydro-6-hydroxy-5-(hydroxyl-methyl)-5,8a-dimethyl-2-methylenenaphthyl]ethylidene)dihydro-4-hydrofuran-2(3H)-one) contained an anti-fatigue agents, pharmaceutical compositions, food, or drink (hereinafter, they are sometimes referred to simply as "composition of the present invention") of the present invention as an active ingredient is a known compound represented by Formula (I) below.

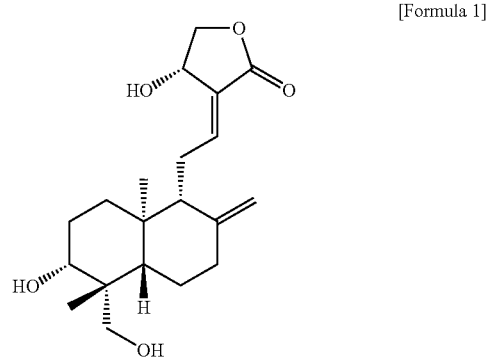 [SMILES: C=C1CC[C@@H]2[C@](C)(CO)[C@H](O)CC[C@@]2(C)[C@@H]1C/C=C1/C(=O)OC[C@H]1O]

[Formula 1]

In this Specification, the wording "containing andrographolide as an active ingredient" indicates that andrographolide, andrographolide derivatives, stereoisomers thereof, polymorphs thereof (hereinafter, they are sometimes referred to as "andrographolides") can be contained either alone or in combination of two or more, as long as a desired effect is produced.

Andrographolide is easily obtained either by extracting it from, for instance, Andrographis paniculata (Senshinren, Andrographis, Andrographis paniculata), which is an acanthaceae plant, and then purifying it, or purchasing a commercially available product. A concrete and exemplary ways of the extraction and purification to obtain andrographolide includes grinding dried Andrographis paniculata, extracting it one after another with methanol, hexane, or the like to obtain extracts, and then purifying the extracts by column chromatography or the like. Concrete and exemplary products that are commercially available include "andrographolide" sold by Wako Pure Chemical Industries, Ltd., Aldrich corp., Sigma, and Calbiochem.

Any of the extracts, the purified products, the synthetics, and the commercially-available products can be used as the andrographolides in the present invention. Extracts of plants containing andrographolides or the like can also be used as the andrographolides in the present invention. For instance, Andrographis paniculata is known to contain andrographolide, deoxyandrographolide, neoandrographolide, homoandrographolide, andrographan, andrographon, andrographosterin, and the like in its leaves, andrographolide, andrographin, and the like in its roots, and 14-deoxy-11-oxoandrographolide, 14-deoxy-11,12-didehydroandrographolide in its entire body (*Chuyaku daijiten*, Vol. 3, the first impression of the first edition issued on Dec. 10, 1985).

The andrographolides that are to be contained in the composition of the present invention can be either used in the form of pharmaceutically acceptable salts or administered in a form (prodrug) that is metabolized in vivo into andrographolide. Examples of acids that form such salts include: inorganic acids such as hydrochloric acid, hydrobromic acid, sulfuric acid, nitric acid, phosphoric acid, and boric acid; and organic acids such as formic acid, acetic acid, propionic acid, trifluoroacetic acid, oxalic acid, succinic acid, maleic acid, fumaric acid, lactic acid, malic acid, tartaric acid, citric acid, salicylic acid, gallic acid, aspartic acid, methane sulfonic acid, trifluoromethane sulfonic acid, benzene sulfonic acid, and p-toluene sulfonic acid. One of them or a combination of two or more of them can be used.

(Alpha-Lipoic Acid)

Neither origin of alpha-lipoic acid (thioctic acid, 1,2-dithiolane-3-pentanoic acid) that can be contained in the composition of the present invention as an active ingredient nor how it is produced is particularly limited, as long as it can be taken in or eaten as a pharmaceutical drug, food, or drink and produces an effect of enhancing anti-fatigue action when it is combined with andrographolide. Further, any of D-configurations, L-configurations, and racemic modifications can be employed, and commercially-available racemic modifications or the like that are easy to obtain can be used.

Alpha-lipoic acid is a substance that is biosynthesized in a body. It exists in most of the cells in a body and plays an important role as a coenzyme that catalyzes oxidative decarbonizing reaction of pyruvic acid, alpha-ketoglutaric acid, and the like in energy metabolism. Alpha-lipoic acid is also known to have an antioxidative property and to contribute to reproduction of endogenous antioxidative agents such as vitamin C, vitamin E, CoQ10, and glutathione.

The alpha-lipoic acid that is to be contained in the composition of the present invention can be either used in the form of pharmaceutically acceptable salts or administered in a form (prodrug) that is metabolized in vivo into alpha-lipoic acid. It is also possible to use the alpha-lipoic acid in the form of various derivatives. Examples of the salts of the alpha-lipoic acid include alkali metal salts, such as sodium salts and potassium salts, and amine salts, and ammonium salts. Examples of derivatives of the alpha-lipoic acid include alkyl or alkenyl esters, amides, dihydrolipoic acids, which are reductants, or alkyl or alkenyl esters thereof, amides, and the like. In the present invention, one of them or a combination of two or more of them can be selected and used.

The inventors of the present invention found that an intake of the andrographolide produced considerable anti-fatigue action and that the anti-fatigue action was enhanced synergistically if the andrographolide was taken in combination with a predetermined amount of alpha-lipoic acid. Compositions having anti-fatigue action are useful for preventing or treating fatigue-related illnesses or conditions.

In the present invention, "fatigue" means temporary phenomenon of decrease in physical, mental and/or organ performance that is observed when physical and/or mental stress is applied continuously. This decrease in performance means qualitative or quantitative decrease in physical, mental and/or organ working capacity. The fatigue includes the phenomenon of decrease in performance that is caused by a combination of mental fatigue (e.g. general lassitude, feeling of weakness, diminished ability to concentrate, disinclination, induction of drowsiness) associated with physical fatigue, organ fatigue associated with mental fatigue, and the like.

The "anti-fatigue agent" that the present invention provides is a composition having "anti-fatigue action". In this Specification, the wording "anti-fatigue action" means action to prevent the fatigue, reduce the fatigue, or recover from the fatigue. Concretely, the "anti-fatigue action" includes: lengthening duration of operation of exercised or worked body parts (the worked body parts mean body parts that worked to fulfill functions, including brain and internal organs) (preventing the duration from shortening); reducing changes in fatigue substances at the same amount of exercise or work (improvement in endurance, enhancement of body strength, reduction of fatigue); improving a state in which fatigue is felt in brain, nerves, or internal organs although body parts having exercised or worked are not fatigued; and promoting recovery of exercised or worked body parts from a fatigue state to a normal state. The endurance includes all physical endurance, mental endurance, and organ endurance, and it means an ability to maintain a certain state of exercise. This anti-fatigue action brings, for instance, the following states: "it becomes possible to swim for a long period of time", "no fatigued is felt even after a long period of work", and "no fatigue remains in everyday life".

In this Specification, the wording "fatigue-related illnesses or conditions" means the fatigue-related illnesses or conditions described above, including illnesses or conditions that relate to physical fatigue, mental fatigue, and organ fatigue. Examples of the "fatigue-related illnesses or conditions" include chronic fatigue syndrome, overwork, muscle fatigue, fatigue from lack of sleep, fatigue from stress, and liver fatigue. Combinations of two or more of them are also included in the examples. Primary symptoms of the chronic fatigue syndrome are long-term general feeling of tiredness, lassitude, low grade fever, lymph node swelling, muscle ache, arthralgia, psychoneurotic symptoms, and the like, which symptoms continue so long that daily activities are interfered. According to the diagnostic criteria of the US Center for Disease Control and Prevention (CDC) for chronic fatigue syndrome (CFS), a feature of pathological chronic fatigue is thought that it is accompanied by physical and/or mental symptoms such as: low grade fever or chill; throat pain; swollen lymph nodes of a neck or in an underarm; feeling of weakness with an unknown cause; muscle pain or discomfort; general lassitude that continue for 24 hours or longer after light exercise; cephalalgia; arthralgia; psychoneurotic symptoms (photophobia, transient scotoma, forgetfulness, irritability, confusion, diminished ability to think, diminished ability to concentrate, depression); and/or sleep disorder (insomnia or hypersomnia). Accordingly, the foregoing symptoms are also encompassed within the "fatigue-related conditions or illnesses" of the present invention.

In this Specification, preventing or treating illnesses or conditions includes preventing the illnesses or conditions from becoming worse, improving and relieving the illnesses or conditions to return to a normal state, and preventing the illnesses or conditions.

Effect of a test substance on fatigue can be examined in various ways that are known among persons skilled in the art, such as measuring endurance and asking a patient about recovery from sensory fatigue, in combination with administration of the test substance. The inventors of the present invention examined the effect of the composition of the present invention on fatigue by conducting the following tests.

The first test is measurement of a swimming time in a water-immersion and sleep-disturbance test. This is described in detail below in Example 1. Mice raised in an environment, such as a water-immersed environment, where they were not allowed to take enough sleep or to take a comfortable posture so that they could take neither physical nor mental rest were weighted and forced to swim, and a length of time that passed until noses of the mice sank under the water for a period of 10 seconds or longer was measured (weight-loaded forced swimming test) to determine their fatigue level.

There is a report saying that it is considerably difficult to establish a fatigue model animal because animals are highly adaptive to a variety of light fatigue and, when given a combination of light fatigue every day, they become resistant to the fatigue. With rats kept immersed in water, however, reduction in glucose consumption at a limited area of brain such as frontal lobe, change in brain monoamine level (Brain 21 (2004) Vol. 7, No. 1, pp. 41-45), change in fatigue-related genes in brain and liver, and the like were observed, so that the rats are recognized as a fatigue model (Journal of Neurochemistry (2005) 95, 1156-1166) (Biochemical and Biophysical Research Communications (2007) 353, 1068-1073). Further, the water-immersed rats were returned to normal rearing, and how they recovered was observed. In this observation, the swimming time in the weight-loaded forced swimming test became longer in proportion to an extended resting period of the water-immersed rats (normal rearing period), and the corresponding change in an amount of brain fractionated monoamine was also observed.

That is to say, since this animal model is a physical and mental fatigue model as well as an organ fatigue model described below, anti-fatigue action against physical and/or mental fatigue would be confirmed if the swimming time becomes longer as a result of administration of the test substance. Such anti-fatigue action is considered to be involved in reduction in fatigue stress, maintenance of physical energy under fatigue conditions (enhancement of body strength), improvement in endurance, and the like.

The second test is measurement of liver fatigue. This is described in detail below in Example 2. In the case of the above model reared in the environment, such as a water-immersed environment, in which the rats are not allowed to have an enough sleep or to take a comfortable posture, fatigue symptoms were observed in the entire body. In a liver of this model, GOT and GPT levels increased, compared with those of a normally-reared group. GOT (glutamic oxalacetic transaminase) and GPT (glutamic pyruvic transaminase), which are enzymes present in hepatic cells, are known to escape into blood when hepatic cells are damaged. Therefore, a level of damage on the liver is determined by measuring GOT and GPT in blood. Further, it was revealed that lipid peroxide in liver increased in this model (measurement was based on TBARS, an amount of thiobarbituric acid reactive substances). It is inferred that the long-term general fatigue condition caused alteration in liver function, disruption of oxygen reduction system balance, and the like to result in accumulation of lipid peroxide. This is considered to support the fact that this model is an organ fatigue model.

That is to say, since this animal model is also an organ fatigue model, anti-fatigue action against organ fatigue would be confirmed if it is observed that administration of the test substance, for instance, returns a changed organ fatigue marker, such as GOT, GPT, and TBARS mentioned above, to a normal level and reduces change in the organ markers. Such anti-fatigue action is considered to regulate overall activity of internal organs to condition metabolism, thereby being involved in reduction of physical and mental fatigue stress, maintenance of energy, improvement in endurance, and the like.

The third test is measurement of an amount of spontaneous exercise in a forced exercise test. This is described in detail below in Example 3. Rats were forced to exercise on a treadmill, and thereafter the test substance was administered. Then, the amount of spontaneous exercise of the animal was measured. Since this animal model is an exercise fatigue (physical fatigue) model, anti-fatigue action against physical fatigue would be confirmed if increase in the amount of spontaneous exercise is observed after the administration of the test substance. Such anti-fatigue action is considered to be involved in improving endurance and exercise performance.

The fourth test is measurement of an amount of fatigue substance. This is described in detail below in Example 4. The test is to determine the effect of administration of the test substance on the amount of fatigue substance at the time when physical or mental stress is applied. Since the fatigue substances change according to the type, intensity, duration, or the like of fatigue that is applied, they are not clearly defined as an indicator, but creatine kinase in blood can be named as one of the candidate substances. Creatine kinase is an enzyme that catalyzes high-energy phosphoryl group transfer from creatine phosphate to ADP, and is considered to serve physiological functions of consuming creatine phosphate to supply ATP at the time of massive energy consumption, such as twitching of skeletal muscles upon instantaneous short-term exercise, in an in vivo energy system. Further, it is also known that creatine kinase is contained in the tissues within a living body, and a large amount of creatine kinase is contained especially in muscles. It is also known that, when muscle is fatigued, muscle cells are damaged by chemical and physical (e.g. reactive oxygen) stress, and creatine kinase escapes from the muscle cells into blood. It is therefore said that the level of damage on the muscle can be determined by measuring the creatine kinase activity in blood. Specifically, anti-fatigue action against physical fatigue, especially muscle fatigue, would be confirmed if it is observed that increase in creatine kinase activity is reduced as a result of administration of the test substance. This anti-fatigue action is considered to reduce damage on muscle and therefore enhance body strength and muscle strength.

In any of the tests above, the anti-fatigue action of the test substance can be confirmed in various points of view by appropriately arranging the timing of administration of the test substance and application of fatigue stress. Specifically: (i) whether the test substance reduces fatigue stress can be confirmed by administering the test substance during the application of the fatigue stress; (ii) whether the test substance promotes recovery from fatigue can be confirmed by administering the test substance after the application of the fatigue stress; and (iii) whether the test substance prevents or reduces fatigue can be confirmed by administering the test substance and thereafter applying the fatigue stress.

In all of the tests above, i.e., the water-immersion and sleep-disturbance test, the measurement of organ fatigue, the forced exercise test, and the measurement of the amount of fatigue substance, anti-fatigue action was confirmed after the intake of andrographolide. Further, synergistic improvement in anti-fatigue action was confirmed in the water-immersion and sleep-disturbance test after the intake of andrographolide in combination with a predetermined amount of alpha-lipoic acid. The foregoing results indicate that the andrographolide and the combination of andrographolide and alpha-lipoic acid not only have anti-fatigue action, i.e., action to prevent fatigue, action to reduce fatigue, and action to recover from fatigue, but also are useful for preventing or treating fatigue-related illnesses or conditions such as chronic fatigue syndrome.

As it is apparent from the Examples described below, the composition of the present invention reduces fatigue stress when it is taken in during the fatigue stress, promotes recovery from fatigue when it is taken in after the fatigue, or prevents or reduces fatigue stress when it is taken in before the fatigue stress. Thus, the timing of administration of the composition of the present invention can be determined appropriately according to a desired effect. The composition of the present invention can be taken in each time when the effect is desired, or it can be taken in on a regular basis to obtain the effect. In other words, the composition of the present invention can be taken in not only when physical fatigue is felt at the time of doing muscle exercise such as sports, or when mental fatigue is felt at the time of doing a continuous task such as calculation, to promote recovery from the fatigue, but also before work, sports, or the like to prevent fatigue. Further, endurance is expected to improve if the composition of the present invention is taken in before or during sports. Furthermore, fatigue and illnesses associated with the fatigue are prevented if the composition of the present invention is taken in on a regular basis.

Andrographis paniculata containing andrographolide has conventionally been taken in orally and is considered to be infinitely safe. It is confirmed that when mice take in 0.5 g/kg of Andrographis paniculata per day for 10 days, no abnormality is observed in growth, appetite, defecation, mental conditions, the number of red blood cells and white blood cells, and numerical values of classification of hemoglobin and white blood cells. It should be noted, however, that there is a report saying that, when an infusion (0.5 g per mouse) or a water extract (1 g of crude drug per mouse) of Andrographis paniculata was injected into abdominal cavities of two mice, they died within 24 hours (*Chuyakudaijiten*, First Issue, Vol. 3). The inventors of the present invention confirmed that when 1000 mg of andrographolide per kilogram of body weight was administered, no abnormality was observed. Accordingly, the andrographolide in the composition of the present invention is an active ingredient that is infinitely safe. Thus the amount of andrographolide to be contained is not particularly limited, as long as the amount is adequate to produce a desired effect and not to be toxic; the amount can be appropriately determined according to targets, pathological condition and the stage of illness, impact on taste (slightly bitter), and other factors.

In the determination that the inventors of the present invention conducted using fatigue animal models such as mice and rats, desired anti-fatigue action was produced by taking in 0.25-200 mg of andrographolide per kilogram of body weight in the case in which andrographolide was taken in either in advance or during fatigue stress to prevent or reduce mental, physical, and organ fatigue. In the case in which andrographolide was taken in to promote recovery from physical fatigue already developed, desired anti-fatigue action was produced by taking in 0.5-8 mg of andrographolide per kilogram of body weight. Accordingly, the amount of andrographolide to be contained in the composition of the present invention is 0.01-500 mg per kilogram of body weight, preferably 0.1-50 mg per kilogram of body weight, more preferably 0.1-10 mg per kilogram of body weight, especially preferably 0.25-10 mg per kilogram of body weight, per daily amount of the composition to be taken by animals including humans. Especially in the case in which andrographolide is to be orally administered to humans (adult) to obtain anti-fatigue action, it is generally suitable to administer 0.1-100 mg of andrographolide, preferably 0.1-50 mg, more preferably 0.1-10 mg, especially preferably 0.25-10 mg, per daily amount of andrographolide to be taken.

Note that if andrographolide is to be mixed in the form of a derivative, a salt, or the like of the andrographolide, the amount of the derivative, the salt, or the like that is to be mixed is determined by converting the amount of the derivative, the salt, or the like into the corresponding amount of the andrographolide and referring to the foregoing amounts.

Alpha-lipoic acid is a substance present in a body. It is applied to pharmaceuticals for supplementation of thioctic acid when a need for the thioctic acid increases (at the time of acute physical fatigue), for subacute necrotizing encephalomyelopathy, and for toxic (streptomycin-induced, kanamycin-induced) and noise-induced (occupational) hearing loss. Alpha-lipoic acid is considered to be infinitely safe. Thus the amount of alpha-lipoic acid to be contained can be appropriately determined according to targets, pathological condition and the stage of illness, impact on taste (slightly bitter), and other factors, as long as the amount is adequate to produce a desired effect and not to be toxic.

In the determination that the inventors of the present invention conducted using the fatigue animal model of mice, anti-fatigue action was produced by taking in 50 mg of alpha-lipoic acid per kilogram of body weight in the case in which the alpha-lipoic acid was administered alone during fatigue stress to prevent and/or reduce mental and physical fatigue, and synergistic anti-fatigue action was produced by taking in 50 mg of alpha-lipoic acid per kilogram of body weight in the case in which the alpha-lipoic acid was administered in combination with andrographolide (0.25 mg per kilogram of body weight) during fatigue stress to prevent and/or reduce mental and physical fatigue.

Given the foregoing, it is preferable that the composition of the present invention contain the alpha-lipoic acid such that 1-200 mg, preferably 1-100 mg, of alpha-lipoic acid per kilogram of body weight of the target is administered per daily amount of the composition to be taken in. Especially when the alpha-lipoic acid is to be orally administered to a human (adult) to obtain the anti-fatigue action, it is generally suitable that approximately 10-400 mg, preferably 10-200 mg, more preferably 10-100 mg, of the alpha-lipoic acid is administered per daily amount of the composition to be taken in.

In other words, the composition of the present invention contains, per daily amount of the composition to be taken by animals including humans, 0.01-500 mg of andrographolide per kilogram of body weight, preferably 0.1-50 mg per kilogram of body weight, more preferably 0.1-10 mg per kilogram of body weight, especially preferably 0.25-10 mg per kilogram of body weight, and further contains 1-200 mg, preferably 1-100 mg, of the alpha-lipoic acid per kilogram of body weight in the respective cases. Alternatively, the composition of the present invention contains, per daily amount of the anti-fatigue agent to be taken by a human (adult), 0.1-100 mg of andrographolide, preferably 0.1-50 mg, more preferably 0.1-10 mg, especially preferably 0.25-10 mg, and further contains 10-400 mg, preferably 10-200 mg, more preferably 10-100 mg, of the alpha-lipoic acid in the respective cases.

Daily intake can be either taken a single time or separately taken multiple times (e.g., 2 or 3 times). Specifically, the composition of the present invention contains, per amount of the composition to be taken by a human (adult) at one time, 0.03-50 mg, preferably 0.05-25 mg, more preferably 0.03-5 mg, especially preferably 0.13-5 mg, of andrographolide and further contains 3-200 mg, preferably 3-100 mg, more preferably 3-50 mg, of alpha-lipoic acid in the respective cases.

Note that if the alpha-lipoic acid is to be mixed in the form of a derivative, a salt, or the like of the alpha-lipoic acid, the amount of the derivative, the salt, or the like that is to be mixed is determined by converting the amount of the derivative, the salt, or the like into the corresponding amount of the alpha-lipoic acid and referring to the foregoing amounts.

The composition of the present invention produces anti-fatigue action not only with respect to humans but also to livestock for labor, hound dogs, racehoses, pet animals, and other animals.

Andrographolide has high stability to pH, moisture, oxidation, light, heat, and the like. Thus andrographolide can be contained in the composition of the present invention without being processed or made into various forms according to the purpose by use of methods that are publicly known among people skilled in the art; for instance, it can be made into food, drink, seasoning, alcoholic beverages, functional food, pharmaceuticals, or the like. Especially the composition of the present invention can be made into pharmaceuticals for oral administration or food (e.g., functional food, dietary supplement, food with nutrient function, food for specified use, food for specified health use, nutritional supplement, health food, food for diet therapy, general health food, supplements).

Concrete examples of the forms include solid, semi-liquid, and liquid. Examples of the solid food include general food and health food that are in the form of candies, drops, lozenges, chewing gum, biscuits, sheets, pills such as tablets and capsules, or granulated powder. Examples of the semi-liquid food include general food and health food that are in the form of paste, jelly, or gel. Examples of the liquid food include general food and health food that are in the form of juice, soft drink, tea, energy drink (e.g., sports drink), or alcohol beverages.

In the case in which the composition of the present invention further contains the alpha-lipoic acid, the alpha-lipoic acid can be contained in the same administration unit as the andrographolide, or the active ingredients may be contained in different administration units.

If necessary, the composition of the present invention may contain an additive and/or a ingredient used in common pharmaceutical compositions, food, and drink, in addition to the andrographolides and the alpha-lipoic acids. Examples of the additive and/or the ingredient include vitamins, such as vitamin E and vitamin C, sugars, diluents, disintegrants, emulsifiers, tonicity agents, buffering agents, solubilization agents, preservatives, stabilizing agents, antioxidant agents, coloring agents, flavors, coagulants, pH adjusters, thickeners, essence powders, crude drugs, and inorganic salts.

Kinds of active ingredients, specific purpose of use of the composition of the present invention (e.g., to improve endurance, to enhance body strength, to reduce fatigue, to promote recovery from fatigue, to relieve chronic fatigue, to relieve organ fatigue, and to maintain health), and/or specific ways of using the composition of the present invention (e.g., amount of intake, number of intake, way of intake) can be labeled on a package, a container, or an instruction of the composition of the present invention.

As it is apparent from the Examples described below, the inventors of the present invention confirmed that andrographolide and the combination of andrographolide and alpha-lipoic acid have effect on not only physical fatigue but also mental and organ fatigue. It is therefore expected that various body strength enhancing action, endurance improving action, and anti-fatigue action are produced additionally or synergistically if andrographolide or the combination of andrographolide and alpha-lipoic acid is taken in orally in combination with, for instance, the conventional compositions of Patent Literatures 1-5, such as compositions having conventional body strength enhancing action and fatigue recovery promoting action and compositions for the purpose of supplementing nutrition at the time of fatigue. Note that the conventional compositions and the andrographolide or the combination of andrographolide and alpha-lipoic acid can be taken in either concurrently or separately.

Examples of other active ingredients that can be contained in the composition of the present invention include: vitamins such as vitamin B1, vitamin B2, vitamin B6, vitamin B12, nicotinic acid, vitamin C, vitamin D, vitamin E, and pantothenic acid; essential amino acids such as valine, leucine, isoleucine, tyrosine, tryptophan, alanine, glutamine, and arginine; minerals such as calcium, magnesium, iron, zinc, and copper; alpha-linolenic acid, EPA, DHA, arachidonic acid, octacosanol, taurine, glucuronic acid, theanine, gamma-aminobutyric acid, CoQ10, L-carnitine, polyphenols, catechins, xanthine derivatives, peptides, and proteins. Note that the composition of the present invention is not limited to those listed above.

The composition of the present invention can be used for beauty care such as wrinkles and skin damage from fatigue. It is known that accumulation of fatigue deteriorates metabolism and consequently causes wrinkles, skin damage and the like.

EXAMPLES

The following describes the present invention, with reference to the Examples. The present invention, however, is not limited to the Examples.

Example 1

Water-Immersion and Sleep-Disturbance Test (Measurement of Swimming Time)

Effect of andrographolide on fatigue from water immersion and sleep disturbance was examined using a partially modified method of Tanaka et al. (Neuroscience Let. 352, 159-162, 2003). Specifically, 8-week-old male Balb/c mice were used as a test animal, and the mice were divided into five groups in such a manner that the groups each had an equal average body weight (5-10 mice per group). Four out of the five groups were reared as water-immersed groups; the groups were kept in cages in such a manner that each of the cages was filled with tap water at 23° C. with a water depth of 7 mm, instead of a floor covering, so that the mice were immersed in water and deprived of sleep. The mice were immersed in water for two days, andrographolide (Aldrich corp., purity 98%) was forcibly administered orally to the mice with doses of 0.5, 2, 8 mg per kilogram of body weight once daily during the two days (water-immersed and andrographolide-administered group). As a control group, one of the groups was immersed in water for two days, and distilled water was forcibly given orally to the group once daily during the two days (water-immersed control group). The remaining one of the five groups was reared as a normally-reared group; this group was kept in a cage with a normal floor covering, and distilled water was forcibly given orally to the group once daily during the two-day rearing (normally-reared control group). After the two days, each of the mice was provided with a weight corresponding to 8% of its body weight, which weight was attached to its tale, and then the mice were forced to swim in a water tank having a diameter of 18 cm and filled with water having a depth of 30 cm. A length of time that passed until the mice sank under water for a period of 10 seconds or longer (swimming time) was measured (weight-loaded forced swimming test).

The swimming time of the mice of the water-immersed group was shorter than that of the mice of the normally-reared group because of fatigue from the water immersion and sleep disturbance. The effect of andrographolide on the fatigue from the water immersion and sleep disturbance was examined by determining recovery of a reduction in the swimming time of the mice of the water-immersed group after the administration of andrographolide. The results are shown in FIG. 1(A). In the figure, "*" indicates that the Student t-test was performed with the significance level of 0.05%, and "**" indicates that the Student t-test was performed with the significance level of 0.01%.

As it is apparent from the results shown in FIG. 1(A), the swimming time of the water-immersed control group shortened considerably, compared with that of the normally-reared control group. On the other hand, the reduction in the swimming time of the water-immersed and andrographolide-administered group was prevented in a dose-dependent manner. This is considered to indicate that fatigue from water immersion and sleep disturbance stress is reduced considerably if andrographolide is administered during the water immersion and sleep disturbance stress.

The same procedure was repeated, except that 0.25 mg of andrographolide per kilogram of body weight was administered once daily. The results are shown in FIG. 1(B). It was confirmed administration of 0.25 mg of andrographolide per kilogram of body weight also prevented reduction in the swimming time. Further, the same procedure was repeated, except that 200 mg of andrographolide per kilogram of body weight was administered once daily. The results are shown in FIG. 1(C). It was confirmed that administration of 200 mg of andrographolide per kilogram of body weight also prevented reduction in the swimming time, and that no toxicity to the mice was observed.

Example 2

Measurement of Liver Fatigue

Effect of andrographolide on fatigue from water immersion and sleep disturbance was examined using a partially modified method of Tanaka et al. (Neuroscience Let. 352, 159-162, 2003). Specifically, 8-week-old male Balb/c mice were used as a test animal, and the mice were divided into three groups in such a manner that the groups each had an equal average body weight (5-10 mice per group). Two out of the three groups were reared as water-immersed groups; the groups were kept in cages each of which was filled with tap water at 23° C. with a water depth of 7 mm, instead of a floor covering, so that the mice were immersed in water and deprived of sleep. The mice were immersed in water for two days, and 8 mg of andrographolide (Aldrich corp., purity 98%) per kilogram of body weight was forcibly administered orally to the mice once daily during the two days (water-immersed and andrographolide-administered group). As a control group, one of the groups was immersed in water for two days, and distilled water was forcibly given orally to the group once daily during the two days (water-immersed control group). The remaining one of the three groups was reared as a normally-reared group; this group was reared in a cage with a normal floor covering, and distilled water was forcibly given orally to the group once daily during the two-day rearing (normally-reared control group). After the two days, blood and liver were taken out of the mice. Blood serum was separated from the blood, and GOT (glutamic oxalacetic transaminase) and GPT (glutamic pyruvic transaminase) in the blood serum were measured with a small-sized biochemistry automatic analyzer (Model 7070, Hitachi High-Technologies Corporation). Further, levels of lipid peroxide from liver were measured as a level of TBARS (thiobarbituric acid reactive substances). As to the TBARS, 1.15% KCl solution was added to a liver in four (w/v) times a liver weight to prepare a sample homogenate with a physcotoron (Niti-on Medical Supply Co., Ltd.). Then, the TBARS levels were measured in accordance with the method of Ohkawa et al. Anal. Biochem. 95. 351-358, 1979. The results are shown in FIGS. 2(A)-2(C). In the figures, "*" indicates that that the Student t-test was performed with the significance level of 0.05%, and "**" indicates that the Student t-test was performed with the significance level of 0.01%.

Figure 2:
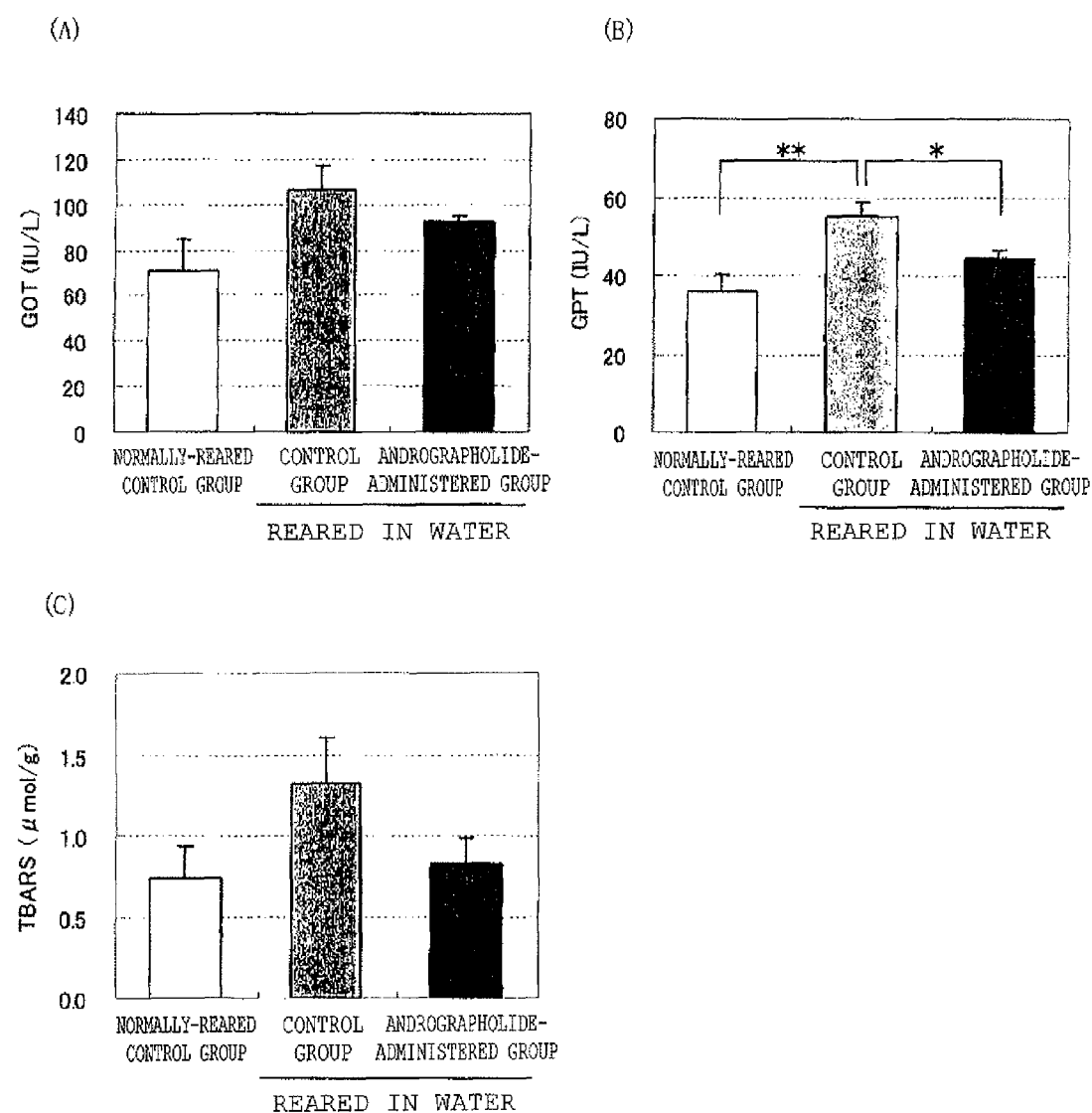
FIG. 2 is a graph showing a relationship between administration of andrographolide and GOT levels in blood serum (A), GPT levels in blood serum (B) and liver TEARS levels (C) after water immersion in Example 2.

As is apparent from the results shown in FIG. 2, the GOT level in the blood serum of the water-immersed control group (FIG. 2(A)), the GPT level in the blood serum (FIG. 2(B)), and the liver TBARS level (FIG. 2(C)) increased considerably, compared with those of the normally-reared control group. On the other hand, the markers were prevented from increasing in the water-immersed and andrographolide-administered group. This is considered to indicate that the liver fatigue from the water immersion and sleep disturbance stress is reduced considerably if andrographolide is administered during the water immersion and sleep disturbance stress.

Example 3

Forced Exercise Test

Six-week-old male Sprague Dawley rats were used as a test animal. On the day before the test was started, the rats were divided into five groups each having eight rats, and all of the rats were deprived of food since the morning of the test day. Four out of the five groups were reared as exercise stress groups; exercise stress (belt speed 10 m/minute, at an angle of gradient of 5%, ascent, 3 hours) was applied to the groups using a treadmill (MK-680, Muromachi Kikai Co., Ltd.). After the exercise stress was finished, 0.5 mg of andrographolide (Aldrich corp., purity 98%) per kilogram of body weight, 2 mg of andrographolide (Aldrich corp., purity 98%) per kilogram of body weight, and 8 mg of andrographolide (Aldrich corp., purity 98%) per kilogram of body weight were forcibly administered orally to the groups, respectively (exercise-stress and andrographolide-administered group). As a control group, distilled water was forcibly given orally to one of the groups after the exercise stress was finished (exercise-stress control group). The remaining one of the five groups was not given the exercise stress, and distilled water was forcibly given orally to this group (control group without exercise stress). Thereafter, the rats were moved into a spontaneous exercise measuring device having an infrared sensor (Supermex, Muromachi Kikai Co., Ltd.), and an amount of spontaneous exercise was measured during a period of 0-2 hours (exploration) and a period of 2-14 hours (dark period).

Figure 3:
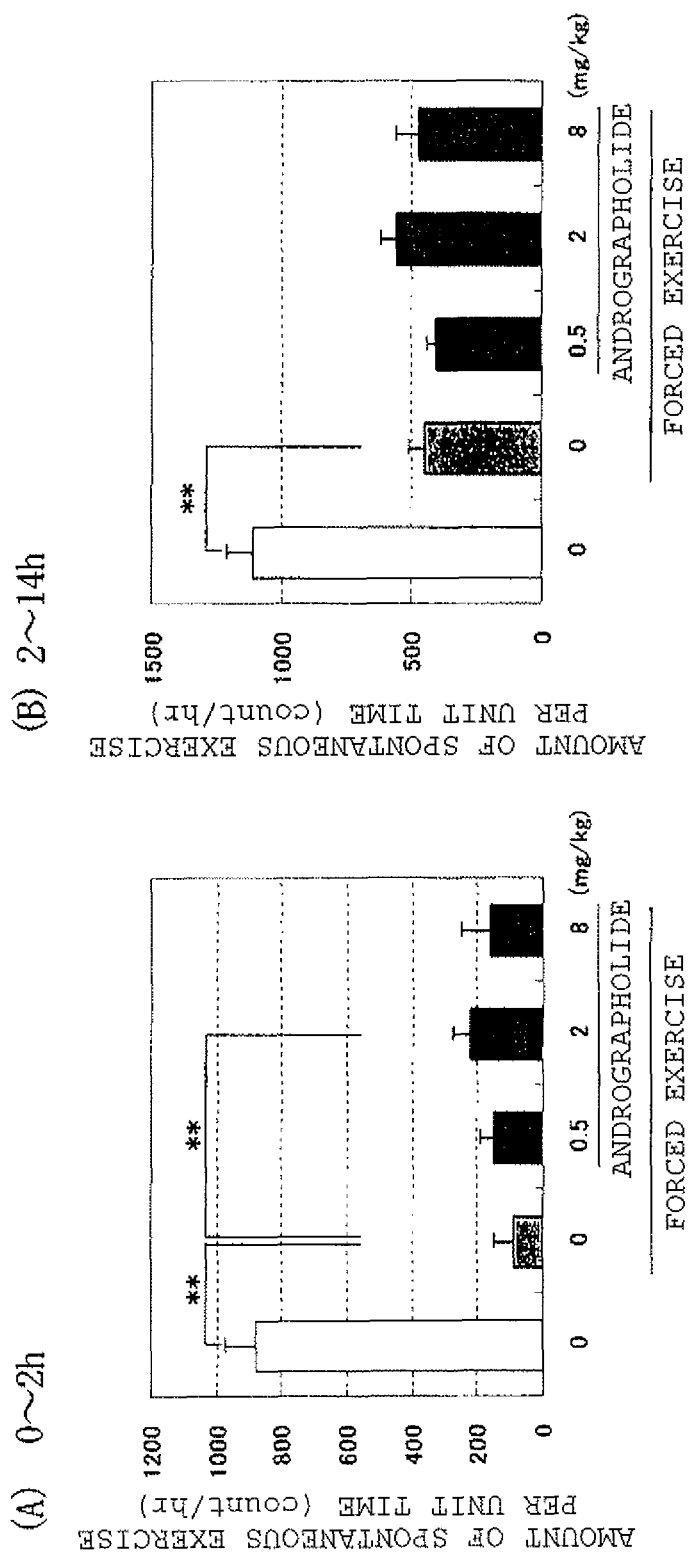
FIG. 3 is a graph showing a relationship between administration of andrographolide and an amount of spontaneous exercise (amount measured during a period of 0-2 hours: exploration (A), amount measured during a period of 2-14 hours: spontaneous exercise (B) during a dark period) after forced exercise in Example 3.

The amount of spontaneous exercise of the rats of the exercise stress group decreased during the exploration (exploration to new environment) and the dark period (spontaneous behavior during an active period in the dark period), compared with that of the rats of the group without exercise stress. This is considered to indicate that the rat model reflects a state of fatigue from exercise stress. The effect of andrographolide on the fatigue from the exercise stress was examined by determining recovery of a reduction in the amount of spontaneous exercise of the rats of the exercise stress group after the administration of andrographolide. The results are shown in FIG. 3. In the figure, "**" indicates that the Student t-test was performed with the significance level of 0.01%. FIG. 3(A) shows the amount of spontaneous exercise during the period of 0-2 hours (exploration). FIG. 3(B) shows the amount of spontaneous exercise during the period of 2-14 hours (dark period). Measurement during the period of first two hours since the measurement was started was separated from that during the period of 2-14 hours, because not only exploration but also excitatory action of the material administered were considered to affect the measurement during the period of first two hours.

As it is apparent from the results shown in FIG. 3, the amount of spontaneous exercise of the exercise-stress control group decreased considerably in all of the periods, compared with that of the control group without exercise stress. Further, in the exercise-stressed and andrographolide-administered group, increase in the amount of spontaneous exercise was observed in the case in which 2 mg of andrographolide per kilogram of body weight was administered. This is considered to indicate that the administration of andrographolide after the exercise stress promotes recovery from fatigue caused by the exercise stress.

Example 4

Measurement of Fatigue Substance in Blood

Muscle fatigue in a living body was determined using creatine kinase levels in blood as a reference index. Six-week-old male Sprague Dawley rats were used as a test animal. A forced-exercise-stress animal was prepared using the method of Example 3 with slight modification. Two days before the forced exercise stress was started, the rats were divided into five groups each having eight rats. With respect to three out of the five groups, 0.5 mg of andrographolide (Aldrich corp., purity 98%) per kilogram of body weight, 2 mg of andrographolide (Aldrich corp., purity 98%) per kilogram of body weight, and 8 mg of andrographolide (Aldrich corp., purity 98%) per kilogram of body weight were forcibly administered orally twice daily, respectively, before the forced exercise stress was started (exercise-stressed and andrographolide-administered group); the administration of andrographolide was done five times in total, including the day on which the forced exercise stress was applied. The remaining two of the five groups served as control groups, and, similarly, distilled water was forcibly given orally to the two groups. On the day of the forced exercise stress, all of the animals were deprived of food after a test sample was administered. No exercise stress was applied to one of the control groups, and distilled water was forcibly administered orally to this group (control group without exercise stress). To the animals of the other four groups, exercise stress (with a belt speed increased gradually from 15 m/minute by 1 m/minute increments and thereafter kept at 25 m/minute for 20 minutes, at an angle of gradient of 10%, ascent) was applied using a treadmill (MK-680, Muromachi Kikai Co., Ltd.). Blood was taken out from a tale vein immediately after the exercise stress, and creatine kinase activity in blood plasma was measured with a biochemistry automatic analyzer (Model 7070, Hitachi High-Technologies Corporation) using an enzyme method.

Creatine kinase activity of the rats of the exercise stress group increased, compared with the rats of the group without exercise stress. This is considered to indicate that muscle fatigue is developed in the rat model as a result of the exercise stress. Effect of administration of andrographolide on muscle fatigue was examined by determining how much increase in creatine kinase activity of the rats of the exercise stress group was prevented when andrographolide was administered. The results are shown in FIG. 4.

Figure 4:
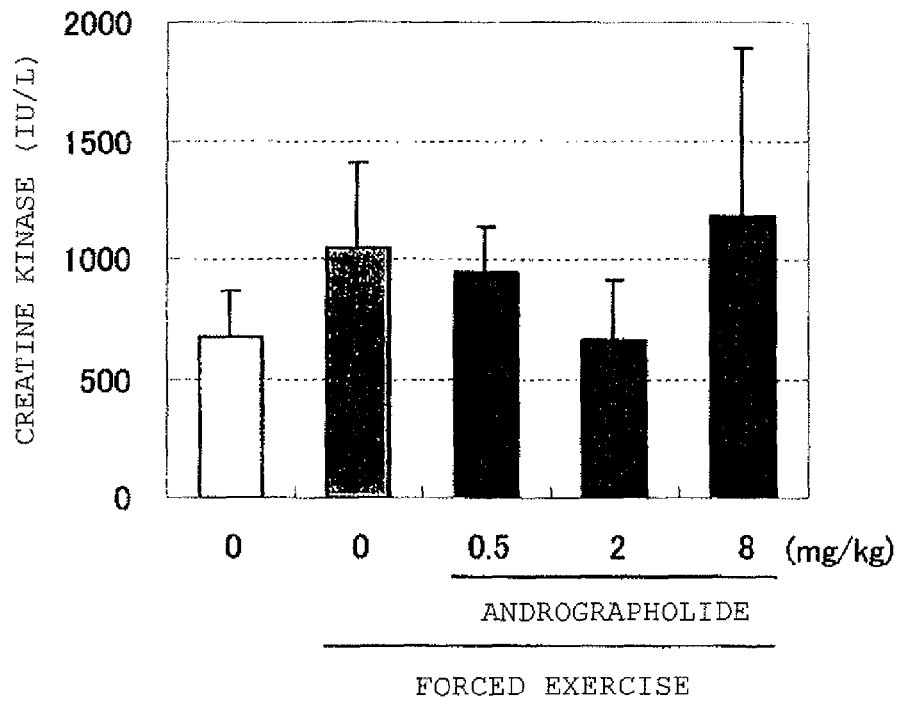
FIG. 4 is a graph showing a relationship between administration of andrographolide and creatine kinase activity in blood after forced exercise in Example 4.

As it is apparent from the results shown in FIG. 4, the creatine kinase activity of the exercise-stress control group increased greatly, compared with that of the control group without exercise stress. On the other hand, decrease in creatine kinase activity was observed in the exercise-stressed and andrographolide-administered group in the case in which 2 mg of andrographolide per kilogram of body weight was administered. This is considered to indicate that muscle fatigue from exercise stress is prevented if andrographolide is administered before the exercise stress.

Example 5

Water-Immersion and Sleep-Disturbance Test with Administration of Andrographolide and/or Alpha-Lipoic Acid In accordance with the procedure described in Example 1, effect on water-immersion and sleep-disturbance fatigue was examined in a case in which andrographolide was administered alone to mice, a case in which alpha-lipoic acid was administered alone to mice, and a case in which a combination of andrographolide and alpha-lipoic acid was administered to mice. Eight-week-old male Balb/c mice were used as a test animal. The mice were divided into five groups in such a manner that the groups each had an equal average body weight (5-6 mice per group). Four out of the five groups served as water-immersed groups, and each of the groups was kept in a cage filled with tap water at 23° C. with a water depth of 7 mm, instead of a floor covering, so that the mice were immersed in water and deprived of sleep. The mice were immersed in water for two days, and andrographolide (Aldrich corp., purity 98%) and/or alpha-lipoic acid were forcibly administered orally to the mice once daily during the two days. The group to which distilled water was forcibly given orally once daily during the two days served as a control group (water-immersed control group). The remaining one of the five groups served as a normally-reared group; this group was kept in a cage with a normal floor covering, and distilled water was forcibly given orally to the group once daily during the two-day rearing (normally-reared control group). After the two days, a weight-loaded forced swimming test was conducted using the same method as that of Example 1.

Example 5

(5a) 0.25 mg of andrographolide per kilogram of body weight, (5b) 50 mg of alpha-lipoic acid per kilogram of body weight, (5c) 0.25 mg of andrographolide per kilogram of body weight+50 mg of alpha-lipoic acid per kilogram of body weight.

Figure 5:
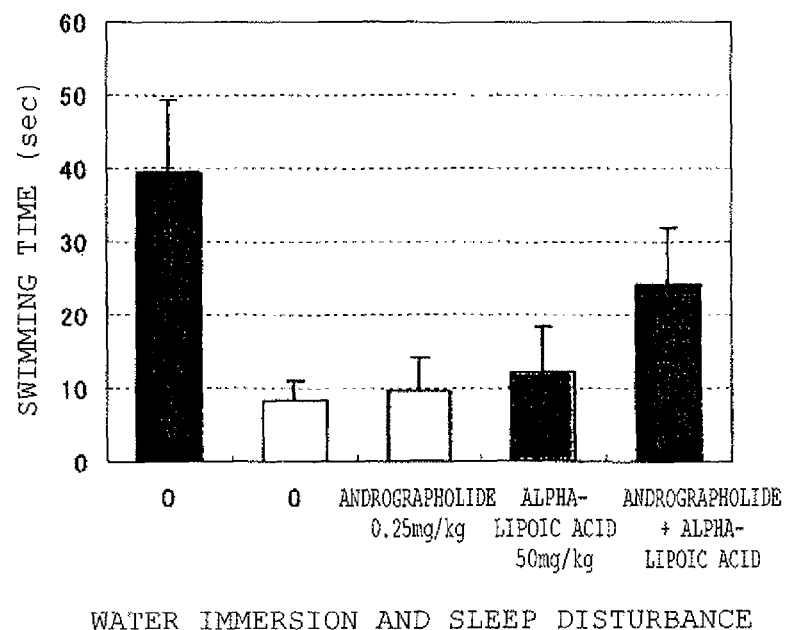
FIG. 5 is a graph showing a relationship between administration of andrographolide and/or alpha-lipoic acid and a swimming time in a weight-loaded forced swimming test after water immersion in Example 5.

The results of Example 5 are shown in FIG. 5. The swimming time of the water-immersed control group shortened considerably, compared with that of the normally-reared control group. On the other hand, the swimming time was prevented from shortening both in the water-immersed group (5a) to which 0.25 mg of andrographolide per kilogram of body weight was administered alone, and the group (5b) to which 50 mg of alpha-lipoic acid per kilogram of body weight was administered alone. With regard to the group to which the combination of andrographolide and alpha-lipoic acid was administered, the swimming time was prevented from shortening synergistically in the group (5c) to which the combination of andrographolide (0.25 mg per kilogram of body weight) and alpha-lipoic acid (50 mg per kilogram of body weight) was administered. Specifically, when the swimming time obtained by subtracting the swimming time of the water-immersed control group from the swimming time of the normally-reared control group was 100%, increase rates of the respective groups were as follows. The swimming time of the group to which andrographolide was administered alone increased by 5%, and the swimming time of the group to which alpha-lipoic acid was administered alone increased by 13%. The swimming time of the group to which the combination of andrographolide and alpha-lipoic acid was administered increased synergistically by 51%.

Example 6

Prescription Example

Formulation Example 1

Capsule (A Human Adult Takes it in a Capsule Per Day.)

Ingredients (1)-(3) below were respectively measured, and a total amount of 200 mg was filled into a capsule.

| (Ingredients) | (mg) |
| --- | --- |
| (1) Andrographolide (Aldrich corp., purity 98%) | 50 |
| (2) Dextrin | 145 |
| (3) Silicon dioxide | 5 |

Formulation Example 2

Drink (A Human Adult Takes it in One Bottle Per Day.)

Ingredients (1)-(5) below were dissolved into ingredient (6) below, and the mixture was put in brown bottles, 120 mL per bottle, and then retort sterilized (121° C., 15 minutes) to give an andrographolide-containing drink.

| (Ingredients) | (%) |
| --- | --- |
| (1) Andrographolide (Aldrich corp., purity 98%) | 0.25 |
| (2) Whey peptide (DVM JAPAN, WE80B) | 1.77 |
| (3) Sodium ascorbate | 0.12 |
| (4) Sucrose | 2.65 |
| (5) Citric acid | 0.21 |
| (6) Purified Water | 95.0 |

Formulation Example 3

Feed for Animals

Ingredients (1)-(8) below were blended to obtain an andrographolide-containing feed for animals.

| (Ingredients) | (weight %) |
| --- | --- |
| (1) Corn | 10-50 |
| (2) Sorghum | 5-30 |
| (3) Barley | 0-20 |
| (4) Soybean cake and meal | 0-40 |
| (5) Bran | 0-20 |
| (6) Mineral | 0-5 |
| (7) Vitamin | 0-3 |
| (8) Andrographolide (Aldrich corp., purity 98%) | 0.001-0.05 |

The invention claimed is:

1. A method of reducing fatigue or recovering from fatigue comprising:
   administering a therapeutically effective amount of an anti-fatigue composition to an animal having a fatigue-related illness or condition,
   wherein the anti-fatigue composition comprises andrographolide and an alpha-lipoic acid,
   wherein the fatigue-related illness or condition is selected from the group consisting of chronic fatigue syndrome, overwork, mental fatigue, and organ fatigue, and
   wherein the animal is a human, and the anti-fatigue composition comprises:
   the andrographolide in an amount of 0.01-500 mg per kilogram of body weight, and
   the alpha-lipoic acid in an amount of 1-200 mg per kilogram of body weight.

2. A method of reducing fatigue or recovering from fatigue comprising:
   administering a therapeutically effective amount of an anti-fatigue composition to an animal having a fatigue-related illness or condition,
   wherein the anti-fatigue composition comprises andrographolide and an alpha-lipoic acid,
   wherein the fatigue-related illness or condition is selected from the group consisting of chronic fatigue syndrome, overwork, mental fatigue, and organ fatigue, and
   wherein the animal is a human adult, and the anti-fatigue composition comprises:
   the andrographolide in a daily amount of 0.1-100 mg, and
   the alpha-lipoic acid in a daily amount of 10-400 mg.

3. The method of claim 1 or 2, wherein the anti-fatigue composition is administered a single time, multiple times, or on a regular basis.

4. The method of claim 1, wherein the animal excludes a human, and
   the anti-fatigue composition is an additive for a pharmaceutical drug, a feed, or a drink.

5. The method of claim 1 or 2, wherein the anti-fatigue composition is contained in a pharmaceutical composition, a food, or a drink for treating the fatigue-related illness or condition.

* * * * *